United States Patent
Johansson Fuenzalida et al.

(10) Patent No.: US 8,742,383 B2
(45) Date of Patent: Jun. 3, 2014

(54) RADIATION PROTECTION DEVICE

(75) Inventors: Max Raúl Johansson Fuenzalida, Santiago (CL); Jorge Andres Bustamante Grant, Santiago (CL); Miguel Enrique San Martin Cancino, Santiago (CL)

(73) Assignee: Surikat S.A., Santiago (CL)

( * ) Notice: Subject to any disclaimer, the term of this patent is extended or adjusted under 35 U.S.C. 154(b) by 0 days.

(21) Appl. No.: 13/573,365

(22) Filed: Sep. 12, 2012

(65) Prior Publication Data
US 2014/0048729 A1    Feb. 20, 2014

Related U.S. Application Data

(60) Provisional application No. 61/626,831, filed on Oct. 4, 2011.

(51) Int. Cl.
*G21F 3/02*    (2006.01)
*G21F 1/02*    (2006.01)
*G21F 3/00*    (2006.01)

(52) U.S. Cl.
CPC   *G21F 1/026* (2013.01); *G21F 3/00* (2013.01); *G21F 3/02* (2013.01)
USPC ............... 250/516.1; 250/505.1; 250/515.1

(58) Field of Classification Search
CPC ........... G21F 1/00; G21F 1/023; G21F 1/026; G21F 1/12; G21F 3/00; G21F 3/02
USPC .......... 250/505.1, 506.1, 515.1, 516.1, 518.1, 250/519.1
See application file for complete search history.

(56) References Cited

U.S. PATENT DOCUMENTS

2004/0041107 A1*   3/2004   Cadwalader et al. ...... 250/519.1

* cited by examiner

*Primary Examiner* — Nicole Ippolito
(74) *Attorney, Agent, or Firm* — John Dodds

(57) ABSTRACT

The present invention relates to the protection of medical patients and personnel from harmful radiation. More specifically, this invention provides a compact, light-weight article to be worn in areas of the body most sensitive to radiation. These include, for example, the pelvic area, the genital and gonad areas, the breast area to guard against radiation to the mammary gland, the neck and throat to protect the thyroid gland, the eye area to protect the crystalline lens.

15 Claims, 3 Drawing Sheets

RADIATION PROTECTION DEVICE

This application claims the benefit of the priority date of the U.S. Provisional Application No. 61/626,831 filed on Oct. 4, 2011

FIELD OF THE INVENTION

The present invention relates to the protection of medical patients and personnel from harmful radiation. More specifically, this invention provides an article to be worn in areas of the body most sensitive to radiation. These include, for example, the pelvic area, the genital and gonad areas, the breast area to guard against radiation to the mammary gland, the neck and throat to protect the thyroid gland, the eye area to protect the crystalline lens. The articles of the present invention are also useful in protecting larger and more general areas such as premature babies, patients exposed to a direct or indirect radiation beam, the fetus and tissues such as epithelium or parenchyma.

BACKGROUND OF THE INVENTION

Ionizing radiation is widely used in industry and medicine, presenting a significant risk to patients and medical personnel. Radiation causes damage to living tissue resulting in burns; moreover, at high exposure sickness, elevated rates of cancer tumor and genetic damage.

Typically, radiation exposure is managed by controlling the factors of exposure time, distance from the source and the use of shields of absorbing materials placed around the radioactive source. Furthermore, radiation is used only when the advantages outweigh the disadvantages; doses are normally kept as low as reasonable.

Shielding is an effective way of reducing radiation and depends upon the density of the material used. For example, lead, the most effective shielding material, has a density of 11.3 g per cubic centimeter as compared to water which has a density of 1.0. The thickness required to reduce radiation by 50% for lead is 0.4 inches, while for water the thickness is 7.2 inches.

Doctors, technicians and patients involved in treatment and diagnosis are subjected to stray radiation even when the apparatus is well screened. To protect themselves against stray radiation, personnel frequently wear protective lead aprons. These heavy lead aprons are not only inconvenient, but also tiring and painful.

Therefore, there remains a need for a shielding, screening or protective device which is light in weight, appropriately sized and easy to use or apply.

SUMMARY OF THE INVENTION

The present invention relates to the protection of medical patients and personnel from harmful radiation. More specifically, this invention provides a compact, light-weight article to be worn in areas of the body most sensitive to radiation. These include, for example, the pelvic area, the genital and gonad areas, the breast area to guard against radiation to the mammary gland, the neck and throat to protect the thyroid gland, the eye area to protect the crystalline lens. The devices of the present invention are also useful in protecting larger and more general areas such as premature babies, patients exposed to a direct or indirect radiation beam, the fetus and tissues such as epithelium or parenchyma.

In another embodiment the present invention provides articles useful in protecting adjacent organs near a radiation emitting source, for example, in brachytherapy procedures. In another embodiment, the devices of the present invention may be located inside the body, blocking irradiation and attenuating body parts that are not relevant to either radiation treatment or diagnosis.

Another application of radio blocking or attenuating elements is at a microscopic level, where barrier elements can be created in clusters of particles, which could protect or reduce the radiation received full or partial organisms, cell clusters, cells, or just parts of an element to radiate.

The elements of radiation protection are configured considering a functional area that attenuates or blocks the radiation and other functional areas that are intended to stick or hold fast the target device and other functional areas that orient or point the correct ways to position and place the device.

Generally, the articles of the present invention are layered constructions, comprising a group of layers having a outer surface, which is oriented in the direction of the radiation source and a wearer surface facing in the opposite direction. The layered construction of the present invention is comprised of a rigid outer layer having an inner surface shaped to contain a radiation attenuating material (RAM); a middle layer having a first side attached to both the inner surface of said outer layer and the radiation attenuating material and a second side attached to the releasable face of an outer layer.

The RAM component comprises at least one of the salts of barium, bismuth, copper, lead, optionally in laminated forms. The RAM may be mixed with excipients, e.g. artificial or natural polymers that confer other desired characteristics such as binding the active ingredients for control of flexibility or rigidity. Excipients may reduce or enhance flexibility, color, aroma, degradation, indicators of use, biodegradation, oxidation, elimination, destruction, crystallization, dehydration, among other characteristics.

In constructing the articles of the present invention the radiation blocking or attenuating material (RAM) can be made by combining, binding, mixing one or more active elements in one or more different states (e.g. powder, liquid, solid, laminated form, etc.), plus a rigid outer layer or container that also functions in shaping or forming the radiation attenuation material when it is present as a liquid over a wide range of viscosity, where the container work as a type of die or mold. This container is comprised of predetermined shaped blisters comprising a rigid plastic including but not limited to PVC, PET, PP, PE, PLA. The radiation blocking material is poured in liquid or semi-liquid form and then solidifies after which a layer of e.g. non woven fabric or other laminated fabric is layed or placed on the solidifying material in direct contact with the radiation blocking material. The fabric is thus adhered to the RAM, optionally with the use of an adhesive.

General Information of Radio Blocking or Attenuating Material

The articles feature a radio opaque material that have the following general characteristics:

1. Capability to attenuate, reduce or block partially or completely ionizing and electromagnetic radiation that is emitted through the material.

2. Capability of being degradable and/or be partially or totally reduced or eliminated in the short term (0-5 years), medium term (5-10 years) or long term (10-100 years). This includes the deterioration of its physical and mechanical properties and a total or partial reduction or elimination of the material as an end of the degradation process.

Partial or total degradation or elimination of the material can occur by the direct or indirect action of different internal and/or external agents including:
1. gases, chemicals, organic or non-organic agents,
2. mono-cellular or multi-cellular microorganisms (such as bacteria, viruses, mould, among others, other organisms such as insects, animals, plants and fungus)
3. temperature
4. atmospheric or ambient pressure
5. lack or excess of solvents (e.g. water or moisture)
6. direct or indirect mechanical fatigue, division or destruction from artificial or natural causes
7. direct or indirect presence of artificial and natural radiation in all its wavelength spectrum including wavelengths from 150 m to 0.0001 nm.

Degradation processes include biodegradation, oxidation, oxo-biodegradation, photo-degradation, photo-oxidation, thermo-degradation, thermo-oxidation, catalysis, dehydration, chain scission of chain molecules, among other forms of degradation processes. Mentioned agents and processes also include additives that can accelerate or decrease speed or effect of certain processes and agents e.g. anti-oxidants and pro-oxidants.

3. Capability to be in an amorphous state of origin and be capable of being molded or formed later in the production processes with the particular feature of being able to attenuate having one or more different thicknesses within the same product and attenuation material.
4. In one version, the material may have an adhesive component, or perform the function of adhesion or binding by its own chemical structure or changes of state of matter that is present.

Detailed Information of Radio Blocking or Attenuating Material

Below is a component list of types of ingredients included to manufacture the radiation attenuating material of the device. This material can be made by one or more of the following items listed below without excluding other types of materials with similar functions and characteristics:
a) Active ingredient(s) or substance(s) with capability to effectively attenuate or block radiation.
b) Structuring compound with and without degradation capability
c) Preservation additive.
d) Defoaming or anti-foaming additive.
e) Lubricant or release agent.
f) Plasticizer or dispersant that increase plasticity or fluidity.
g) Color.
h) Aroma.
i) Taste.
j) User/Usage indicator.
k) Indicator of presence and or location.
l) Fixation system, Bonding/adhesion system.
m) Humectant
n) Heat resistant
o) Freeze resistant a. Active Ingredient(s) or Substance(s) with Capability to Attenuate or Block Radiation.

Radiation can, in theory, be attenuated by any existing material with a sufficient thickness, including water. But today, in referring to use a radiation attenuating material it is meant to use any material or compound that can attenuate radiation with practical use for radiation protection purposes which relates in many cases to a compounds or elements atomic weight and number of electrons.

These radiation attenuating compounds can be metallic or non-metallic found in any form e.g. solid, liquid, powder form, etc. and may be mixed or combined in different proportions.

These may be e.g. salts such as sulfates, oxides, nitrates, etc. of compounds or elements such as lead, bismuth, barium, copper, calcium, tungsten, silver, among other compounds and elements.

b. Structuring Compounds, Stabilizers, Binders, Thickeners, Emulsifiers or Gel-Forming Compounds.

Compounds with degradable capabilities such as:
1. natural polymers such as gels or gelatins from vegetable or animal origin(collagen), hydrogels, organogels and xerogels, aerogels, cellulose derivatives such as Carboxymethylcellulose, Methylcellulose, hydroxypropylcellulose, hydroxypropyl-methylcellulose and ethylmethylcellulose among other compounds with similar characteristics.
2. Bioplastics and organic plastics derived from biomass sources. Among them are plastics based on or derived from:
Polysacharides such as starches (from corn, peas, cereals, rice, wheat, maize, root vegetables, potatoe, cassava, tapioca or from other green plants), glycogen, cellulose, chitin, arabinoxylans, pectins, acidic polysaccharides, Bacterial polysaccharides, Bacterial capsular polysaccharides, among others.
Cellulose esters such as cellulose acetate and its derivatives.
Aliphatic polyesters such as polyhydroxyalkanoate (PHA), Poly-3-hydroxybutyrate (PHB) polyester produced by certain bacteria to process glucose and starch and Polihidroxivalerato (PHV) or Polihidroxiexanoato (PHH, among others.
Thermoplastic Polyesters such as Polylactic acid (PLA) produced from diverse sources such as sugar, or other forms of polylactide such as poly-L-lactide (PLLA), poly-D-lactide (PDLA, among others.
Polyamides such as PA11 and PA12 derived from natural oils.
Polyethylene bioderibados renewable or which present a monomer of ethylene produced by the fermentation of sugar cane, corn.
And any type of polymer referred produced from genetically modified animals and the plants.
3. Other types of polymers such as silicones, petro-polymers (including thermoplastics), organic polymers can be degradable by adding vegetable-based starches in different proportions.

c. Preservatives and Antimicrobial Agents.

The use of preservatives and/or antimicrobial agents both from natural or artificial sources are used to stop or minimize the damage or unwanted modifications of a substance caused by the presence of different types of microorganisms (bacteria, yeasts and molds) which can cause spoilage before or after purchase and use, health problems if ingested, modified product image, among other problems. These preservatives or antimicrobial agents can be used singularly or in combination thereof.

Among the antimicrobial preservatives may be mentioned:
1. Propylparaben
2. Methylparaben
3. Sodium Sulfite
4. Sorbic acid
5. Sodium bisulfite
6. Sodium Sorbate
7. Potassium Sorbate 8. Sodium Benzoate
9. Propylene glycol
10. Any other compound that is present in the International Numbering System (INS) from the INS200 to INS299
11. other compounds that can be used to enhance preservation as in the case of propylene glycol which acts as a solvent and enhancer of methylparaben and propylparaben.
12. Natural antimicrobial preservatives or antimicrobial agents may include essential oils from:
   Cinnamon bark
   Lemongrass
   Thyme (wild)
   Thyme (Red)
   Thyme (geraniol)
   Mint
   Tea Tree
   Coriander
   Lavender (spike)
   Lavender (true)
   Rosemary
   Eucalyptus (radiata)
   Lemon
   Oregano
   Clove
   Paprika d. Defoamer or Anti-Foaming Agent
A chemical additive that reduces and hinders the formation of foam in manufacturing processes including:
   1. Oil based defoamers
   2. Powder defoamers
   3. Water based defoamers
   4. Silicone based defoamers
   5. EO/PO based defoamers
   6. Alkyl polyacrylates
   7. Other similar agents and compounds e. Release Agents or Lubricants
A release agent or lubricant is a compound, agent or chemical used to get a slip effect and/or reduce friction and adhesion power between two surfaces. It can provide a solution in processes involving mold release, die-cast release, plastic release, and tire and web release. These agents or lubricants can be integrated in the material of the surfaces or between the two surfaces to be used or involved. Among known agents are:
   1. Starches
   2. Chalk
   3. Mineral agents such as graphite powder
   4. Water based agents
   5. Oils based agents
   6. Other similar agents and compounds f. Plasticizer or Dispersants are Additives that Increase the Plasticity or Fluidity of the Material to Which they are Added. Known Plasticizers Include:
   1. Glycerin
   2. Sorbitol
   3. Propylene glycol
   4. Gelatin
   5. Starches
   6. Other similar compounds g. Coloring Compounds.
Examples of coloring compounds to used are:
   1. Coloring agents included in the Codex Alimentarius Commission of the International Numbering System (INS) from the INS100 to INS199 with particular emphasis between the INS130 to INS149.
   2. FDA approved food coloring additives such as
      a. FD&C Blue No. 1 Brilliant Blue FCF
      b. FD&C Blue No. 2 Indigotine
      c. FD&C Green No. 3 Fast green FCF
      d. FD&C Red No. 40 Allura Red AC
      e. FD&C Red No. 3 Erythrosine
      f. FD&C Yellow No. 5 Tartrazine
      g. FD&C Yellow No. 6 Sunset Yellow
   3. Other coloring compounds for cosmetics.
   4. Other coloring compounds for medical devices.
   5. Other coloring compounds for industrial products.
   6. Other suitable coloring compounds.

h. Aromas and Scents.

i. Flavorants.
Are the sensory impressions of substances introduces to the mouth, and is determined mainly by the chemical senses of taste and smell. Positive sensory impressions can help to minimize negative impressions from other agents involved in a substance and help the user to use orally a substance without negative impressions. If the radiation protection material ve is to be taken orally the use of these compounds or agents should be in use to make a positive sensory impression.

j. Use-Indicators.
A use-indicator is a compound, chemical or agent that serves to modify the internal or external structure or appearance of a product with intention to indicate the direct or indirect use or opening of a product. Use-indicators are reacting agents that produce a desirable reaction with intention to:
   1. Assure functionality of a product during use period.
   2. Assure users safety.
   3. Assure the product is used by a controlled number of users, e.g. one user (single use).
   4. Among others.

Direct use-indicators can be compounds or agents in a product that reacts to the direct contact with the user, e.g. ph-sensitivity that reacts with the users' skin causing a coloring on the product on the affected or touched area. Another well known direct use-indicator example is to detect an inappropriate use of pools, e.g. urine indicators in the water with a coloring effect.

Indirect use-indicators can be compounds or agents in a product that reacts to the environment, meaning that an opened product can be the same as a product in use. Indirect use-indicators can be sensitive to the environment and air considering presence or absence of:
   1. Gases (e.g. oxygen, CO2, hydrogen)
   2. Temperature
   3. Moisture
   4. Radiation (e.g. UV-light or cosmic radiation)
   5. Particles in suspension (e.g. tar, carbon, formaldehyde, ammonia, arsenic, DDT, cadmium, radon, acetone, among others)
   6. Micro-organisms (e.g. bio-degradation)
   7. Atmospheric pressure Indirect use-indicators are intended to cause alterations of the chemical and/or physical composition of the product or its parts. These indicators can trigger or activate morphological modification processes such as different types of degradation. Degradation is an interaction between the product and the environment e.g. oxidation, dehydration, evaporation, bio-degradation, thermo-degradation, photo-degradation, molecule breaking, etc. Known examples of oxidation indicator are different kinds of vitamins, e.g. vitamin C that reacts with the oxygen in the air and starts to change color with the process. Other processes can involve dehydration or evaporation of solvents where e.g. the presence of water in a material gives flexibility and softness and the dehydration and reduction of its water content (solvent) makes the material stiff and breakable making it difficult to use. The function of these processes is to give the product a factor serves as an indicator of use of the device; the degradation process serves as a disincentive to reuse the product.

Other ways different degradation processes can be manifested by:
- presence or absence of color
- presence or absence of odors or scents
- augmentation or reduction of size or volume
- surface texture modifications
- change of shape and/or proportions
- among others k. Indicator of Presence and or Location.
(to be located as determined by the medical professional)

l. Fixation System or Adhesive Bonding.
Bonding, adhesion or fixation systems can be included in the device by setting:
- mechanical fixation systems:

Adhesive materials fill the voids or pores of the surfaces and hold surfaces together by interlocking, e.g. velcros, clips, sewing, etc.
- chemical fixation systems or adhesive bonding where these produced connections can be soluble or insoluble. The commercially available adhesive can be organic or inorganic and is deposited on one or both substrate surfaces. Examples include the use of synthetic adhesives based on polymers derived from petroleum (e.g. based on poly-vinyl-acetate, ethylenic glues, polyurethane glues, synthetic rubber, cyanoacrylate and anaerobic adhesives, adhesive-based plant derived from potato starch, corn (starch glues, dextrin, natural rubber), adhesives based animal skins of animals (queues gelatin) or dairy (casein glues).
- dispersive fixation systems In dispersive adhesion, also known as physisorption, two materials are held together by van der Waals forces: the attraction between two molecules, each of which has a regions of slight positive and negative charge.
- electrostatic fixation systems Some conducting materials may pass electrons to form a difference in electrical charge at the join. This results in a structure similar to a capacitor and creates an attractive electrostatic force between the materials.
- diffusive fixation systems Some materials may merge at the joint by diffusion. This may occur when the molecules of both materials are mobile and soluble in each other. This would be particularly effective with polymer chains where one end of the molecule diffuses into the other material. It is also the mechanism involved in sintering. When metal or ceramic powders are pressed together and heated, atoms diffuse from one particle to the next. This joins the particles into one.

m. Humectant or Moisturizing Agent
Additive that has the effect of keeping a material moist and can contribute to maintain flexibility and plasticity in a material. Can also be used as a component of antistatic coatings. Known components include:
1. Propylene glycol
2. Water
3. Glycerin
4. Sorbitol
5. Urea and alpha-hydroxy acids (AHA's)
6. Hexylene and Butylene Glycol
7. MP Diol
8. Fatty acids
9. Ceramides
10. Proteins
11. other similar components n. Heat Resistant
1. Chalk
2. Gelatin: higher Bloom grade the better is the heat resistance.

o. Freeze resistant
1. Glycerine
2. glycol p. General Solvent q. Solvent for Type c Ingredients
1. Propylene Glycol
2. Water All components and adhesion systems of the present invention can be of natural or artificial origin; they may be degradable through different processes over time. The degradation processes may be activated by a mechanical action such as compression or division, a chemical action such as catalysts, or by environmental agents e.g. gases, temperature, humidity, radiation, etc.

The material and the container/mold functioning blister may have one or more levels, thicknesses, heights, elevations or bumps to provide a variety protection within the same shield.

The attenuation material includes functional areas related to its physical properties:
- Main adhesion surface: surface in direct contact to K or by indirect contact to K with additional layers in between.
- Main attenuation surface: surface may be related to the thickest part of the material with highest attenuation. It's the surface facing the radiation beam.
- May include an additional release system or agent (B) for better release of the material from package A.
- Heights H: the material may have one or more different heights or thicknesses within the same volume of material.
- Angles α: the material may have one or more angles in relation to the adhesion surface or attenuation surface. The angles are directly relates to thickness differences within the same volume of material.

BRIEF DESCRIPTION OF THE DRAWINGS

The invention will be better understood and objects other than those set forth above will become apparent when consideration is given to the following detailed description thereof. Such description makes reference to the annexed drawings.

In this example the element is a radiolucent foam (invisible on the image) that separates the radiationattenuating material from the zone of interest, reducing partially or all the distortion of the zone of diagnostic interest and therefore improving image quality The image shows an example of a notable decrease of "artifacts" or distortion near the eyes and nose, allows a nincrease of image quality on the zone of paranasal sinuses, improving information contained on the image.

DETAILED DESCRIPTION OF THE INVENTION

The attenuating material can be configured with one, some or all types of ingredients mentioned above. Here is an example of an applied formula with general quantity ranges. Each type of component can potentially be replaced with other similar components mentioned earlier. Table 1.

Here is a preferred version of the same formula with more specific quantities to produce 127.07 grams or 100 ml with a density of 1,2707 g/ml—density changes or differences are expected depending on compounds included and its proportions or quantity percentage. Table 2 a and b The radiation protection material can be used to protect patients and healthcare professionals both in X-ray procedures and CT-scans. In CT-scans it is necessary not to attenuate the full radiation emitted as it is necessary to achieve an image of the patient. This is why CT-scan radiation shields must protect without compromising image quality and causing artifacts which can seriously degrade the quality of computed tomographic (CT) images, sometimes to the point of making them diagnostically unusable.

The use of the radiation attenuating material in CT procedures can be exemplified applying protection or shielding on the eye lens related to a head scan.

Figure 1:
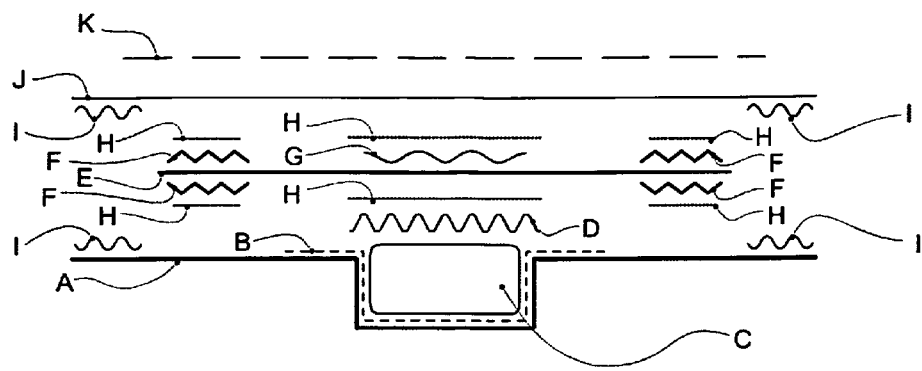
FIG. 1: Schematic cross section of the article of this invention showing its different components and their relationship to each other. These may or may not be all included to define an alternative of the article. The drawing shows lines that do not involve the real morphology but rather showing each component symbolically in order to differentiate between the components.
Figure 2:
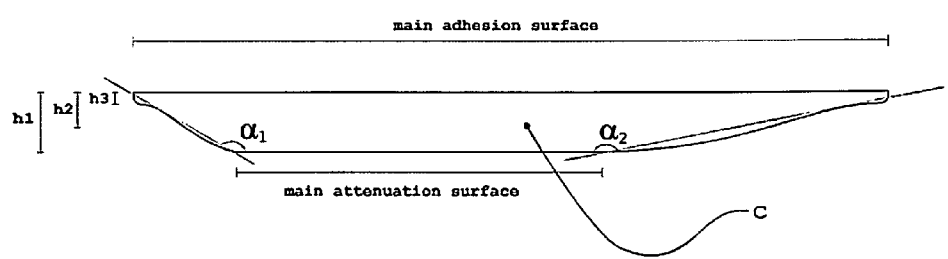
FIG. 2: Schematic cross section of the radiation attenuating material of the present invention showing an example of various heights, angles and thicknesses that may consider differences in radiation attenuation. It can also consider functional areas that can adapt to any surface morphology related or not to the use of the article and it may contain the identification of texts, symbols or marks that provide additional information as part of the general morphology.
Figure 3:
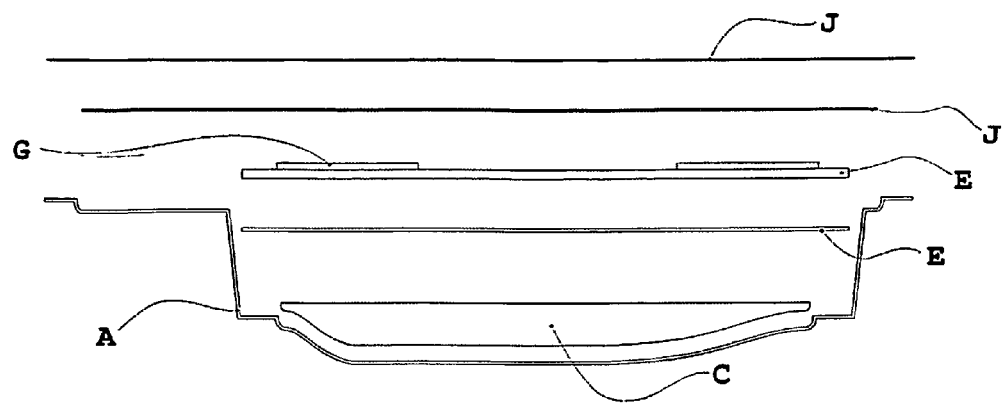
FIG. 3: Cutting sectional diagram of the article of the present invention representing a specific morphology and showing an exemplary form and various functional components. This morphology is showing a possible relationship between this view in cross section and the perspective view in FIG. 4.
Figure 4:
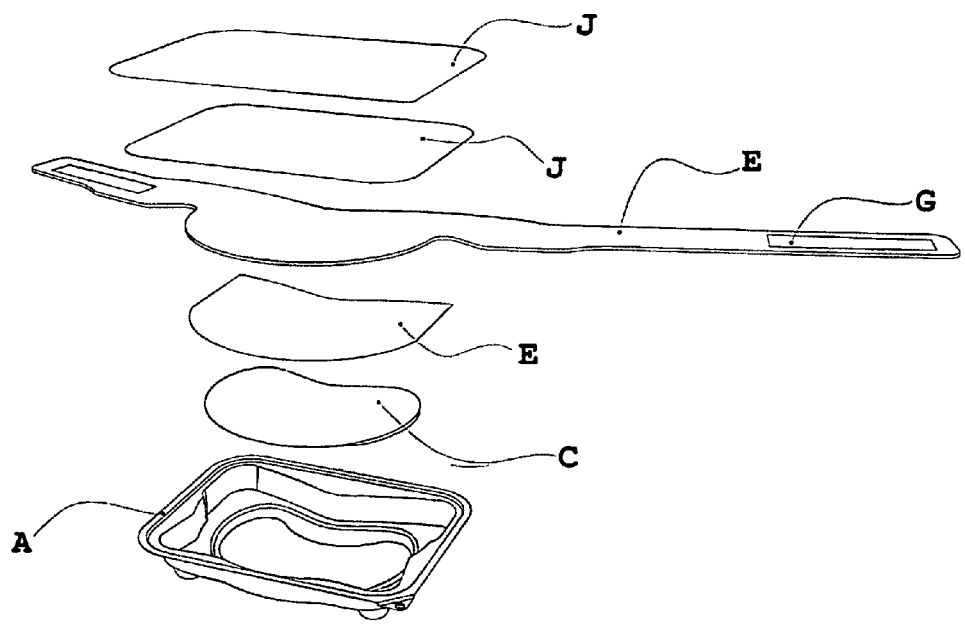
FIG. 4: Schematic diagram in perspective view separately displaying various functional components and layers of the article of the present invention showing an alternative morphology related to FIG. 3.
Figure 5:
FIG. 5: CT brain scan, showing the article of the invention positioned directly over each eye of the patient. It can be observed some image distortion or "white noise" caused by the direct contact between the radiation attenuating material and the patients head. The white superficial "shadows" are caused by the artifact effect. This effect or distortion is not beneficial for a good diagnose.

In the following figures the eye shields are made using a material thickness of 8 mm. In FIG. 5 there is an image of the head scan with eye shields directly placed on the patients' eyes causing artifact on the surface (bright zones next to the eyes).

Figure 6:
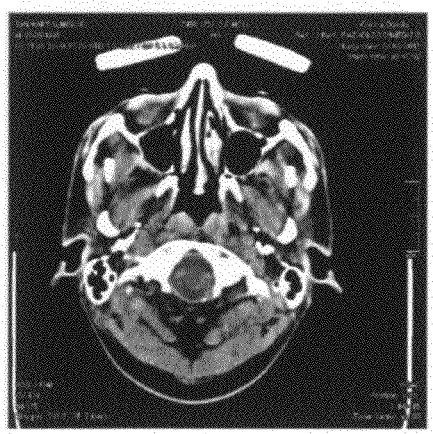
FIG. 6: CT brain scan showing the article of the invention positioned directly over each eye of the patient. It can be observed that elements that allow to reduce, decrease, attenuate or remove the artifacts (white shadows or noise) or distortion of the image are placed between the radioattenuating material and the patients' head.

FIG. 6 shows the same patient with same eye shields but with 10 mm foam between shields and eyes. This reduces drastically the perceived artifact almost to none. This enables the diagnose of superficial areas such as the paranasal sinuses and optical nerves.

Manufacturing Process
the Radiation Attenuating Material

The uniformity level of the "type a" component (active ingredient) is crucial for the radiation attenuation efficiency of the material. The more uniform is the mixture the more uniform is the radiation protection of the material.

To achieve optimum mixing and uniformity it is recommended screening barium sulfate through a ASTM #12 mesh (2 mm in diameter) approximately or preferably a higher ASTM number e.g. ASTM#60 ASTM mesh for better uniformity.

To ensure that the resulting material resists higher atmospheric temperatures it can be recommended to dehydrate the material losing 5%-40% of water (or solvent). This process can give the material a resistance to temperatures above 30° C.

There are several ways or protocols to manufacture the material, but here are described only two examples:

Procedure A:
1. Suspend and mix ingredients "type a", "type b" and "type e" e.g. Barium Sulfate and Corn starch in cold water with high shear agitation.
2. Heat the suspension at 60° C.
3. Add ingredients "type b" e.g. gelatin with constant low shear agitation.
4. Heat ingredients "type q" to 60° C. in suitable and separate container, e.g. propylene glycol.
5. Dissolve ingredients "type c" in heated "type q" (point 4), e.g. dissolve Methyl Paraben and Propyl Paraben in heated Propylen Glycol.
6. Incorporate point 5 solution to the point 3 solution.
7. Mix until completely uniform all ingredients in the mixture.

Procedure B:
1. Heat ingredient "type p" e.g. water (or solvent) to 60° C. in a reactor with low shear agitation
2. Incorporate ingredients "type b", e.g. gelatin slowly with constant stirring.
3. Heat ingredients "type q" in container of adequate capacity.
4. Incorporate ingredients "type c" into the solution of point 3.
5. Incorporate mix of point 4 into reactor of point 1.
6. Sift ingredients "type a", "type b" and "type e" e.g. Barium Sulfate and Corn starch through mesh with ASTM#12 or preferably higher e.g. ASTM #60.
7. Incorporate sifted ingredients of point 6 into gelatin solution into reactor of point 1.
8. Mix ingredients in reactor of point 1 until completely uniform in color or consistency at low shear.

The invention claimed is:

1. A radiation protection article in the form of a layered construction comprising a system of layers having a outer surface oriented in the direction of the radiation source and a wearer surface facing in the opposite direction, said system of layers comprising a rigid outer layer having an inner surface shaped to contain a radiation attenuating material, a middle layer having a first side attached to both the inner surface of said outer layer and the radiation attenuating material and a second side adhesively attached to the releasable face of an outer layer; wherein, said radiation attenuating material is in the form of a moldable gel, viscous liquid or gel forming liquid.

2. A radiation protection article according to claim 1 wherein said radiation attenuating material is comprised of sulfate, oxide or nitrate salts of lead, bismuth, barium, copper, calcium, tungsten or silver in particulate form dispersed in a moldable gel, viscous liquid or gel forming liquid.

3. A radiation protection article according to claim 1 wherein the rigid outer layer is comprised of PVC, PET, PP, PE or PLA.

4. A method of using the radiation protection article of claim 1 wherein said article is attached to a wearers clothing or body part by means of an adhesive or Velcro attachment system.

5. A radiation protection article according to claim 1 wherein said radiation attenuating material has the capability to degrade due to its chemical composition and its capability to interact with the environment where degradation reduces or eliminates said radiation attenuation material in a short term (0-5 years), medium-term (5-10 years) or long-term (10-100 years).

6. A radiation protection article according to claim 1 wherein said radiation attenuating material has the capability to attenuate, reduce or block partially or completely ionizing and electromagnetic radiation that is emitted through the material.

7. A radiation protection article according to claim 1 wherein said radiation attenuating material has the capability to be in an amorphous state of origin and capable of being molded or formed later in the production processes, thus enabling the material to take a specific shape and be in a solid-state of matter.

8. A radiation protection article according to claim 1 that includes a radiation protection material and other layers and parts that are comprised of materials designed to be used for a limited number of uses or a limited amount of time.

9. A radiation protection article according to claim 1 wherein said radiation attenuating material contains one or more different thicknesses within the same product, said attenuation material having the capability to attenuate radiation that passes through the material to a variable way with more or less attenuation with the same shield.

10. A radiation protection article according to claim 1 wherein said radiation attenuated material is comprised of one or more angles in relation to the adhesion surface or the attenuation surface, wherein said angles are directly related to thickness differences within the volume of material.

11. A radiation protection article according to claim 1 wherein said radiation attenuating material is used in single-use or single-user radiation shields in order to improve the hygiene level and avoid cross contamination between shield users.

12. A radiation protection article according to claim 1 wherein said radiation attenuating material has a main adhesion surface which is in direct or indirect contact with additional layers.

13. A radiation protection article according to claim 1 wherein said radiation attenuating material is comprised of a main attenuation surface that is related to the thickest part of the material with highest attenuation rate and is facing the radiation beam.

14. A radiation protection article according to claim 1 wherein said radiation attenuating material is comprised of additional release systems or agents for better release of the material from its package.

15. A method of manufacturing the radiation protection material of claim 1, wherein said material is formed in the liquid state and subsequently poured into a pre-shaped mold.

\* \* \* \* \*